United States Patent
Yoo et al.

(10) Patent No.: US 10,307,259 B2
(45) Date of Patent: Jun. 4, 2019

(54) ARTIFICIAL KNEE JOINT CAPABLE OF PREVENTING DISLOCATION OF THIGHBONE COUPLING MEMBER

(71) Applicant: Corentec Co., Ltd., Cheonan-su, Chungcheongnam-do (KR)

(72) Inventors: Oui-Sik Yoo, Seoul (KR); Jung-Woo Seo, Seoul (KR); Jae-Won Kim, Seoul (KR); Goon-Hee Lee, Seoul (KR); Doo-Hum Sun, Seoul (KR); Yong-Sik Kim, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 24 days.

(21) Appl. No.: 15/524,168

(22) PCT Filed: Oct. 8, 2015

(86) PCT No.: PCT/KR2015/010666
§ 371 (c)(1),
(2) Date: May 3, 2017

(87) PCT Pub. No.: WO2016/072629
PCT Pub. Date: May 12, 2016

(65) Prior Publication Data
US 2017/0333196 A1    Nov. 23, 2017

(30) Foreign Application Priority Data
Nov. 7, 2014    (KR) .......................... 10-2014-0154786

(51) Int. Cl.
*A61F 2/38*    (2006.01)
*A61F 2/30*    (2006.01)

(52) U.S. Cl.
CPC .............. *A61F 2/3886* (2013.01); *A61F 2/38* (2013.01); *A61F 2/389* (2013.01); *A61F 2/3836* (2013.01); *A61F 2002/30878* (2013.01)

(58) Field of Classification Search
CPC ........ A61F 2/38; A61F 2/3836; A61F 2/3859; A61F 2/389; A61F 2/3886
See application file for complete search history.

(56) References Cited

U.S. PATENT DOCUMENTS

| | | | |
|---|---|---|---|
| 5,147,405 A | 7/1992 | Van Zile | |
| 6,558,426 B1 | 5/2003 | Masini | |

(Continued)

FOREIGN PATENT DOCUMENTS

| | | |
|---|---|---|
| KR | 10-2012-0124927 A | 11/2012 |
| KR | 10-2013-0102034 A | 9/2013 |

OTHER PUBLICATIONS

International Search Report and Written Opinion dated Feb. 5, 2016, issued in PCT Application No. PCT/KR2015/010666, filed Oct. 8, 2015.

*Primary Examiner* — Brian A Dukert
(74) *Attorney, Agent, or Firm* — Workman Nydegger

(57) ABSTRACT

An artificial knee joint, which includes an upper surface at which a post performs a motion relative to a cam of the thighbone coupling member, is configured such that a radius of curvature of an upper curved surface extending posteriorly from the upper surface is larger than that of a lower curved surface, so as to prevent the cam of the thighbone coupling member from deviating from an inflection point existing between the upper curved surface and the lower curved surface, and is configured such that the upper surface is inclined at a predetermined angle, so as to allow the thighbone coupling member to be restored while naturally descending along the upper surface even when the thighbone (Continued)

coupling member is dislocated, thereby increasing a jump distance without increasing an amount of bone to be cut.

6 Claims, 10 Drawing Sheets

(56) References Cited

U.S. PATENT DOCUMENTS

| | | | |
|---|---|---|---|
| 2009/0326666 A1* | 12/2009 | Wyss | A61F 2/3886 623/20.29 |
| 2013/0190884 A1 | 7/2013 | Hashida | |
| 2014/0200673 A1 | 7/2014 | Hashida | |

* cited by examiner

ARTIFICIAL KNEE JOINT CAPABLE OF PREVENTING DISLOCATION OF THIGHBONE COUPLING MEMBER

TECHNICAL FIELD

The present invention relates generally to an artificial knee joint capable of preventing dislocation of a thighbone coupling member, the artificial knee joint including a thighbone coupling member, and a bearing member. More particularly, the present invention relates to an artificial knee joint, which includes an upper surface at which a post performs a motion relative to a cam of the thighbone coupling member, is configured such that a radius of curvature of an upper curved surface extending posteriorly from the upper surface is larger than that of a lower curved surface, so as to prevent the cam of the thighbone coupling member from deviating from an inflection point existing between the upper curved surface and the lower curved surface, and is configured such that the upper surface is inclined at a predetermined angle, so as to allow the thighbone coupling member to be restored while naturally descending along the upper surface even when the thighbone coupling member is dislocated, thereby increasing a jump distance without increasing an amount of bone to be cut.

BACKGROUND ART

When a human knee is bent or the body is turned, a joint surface of the knee between the femur and the tibia performs a rotational motion in an axial direction, or performs a translational motion on abduction or adduction, in the sagittal or coronal plane, and the above mechanism of knee motion is to absorb or control the force generated during exercise with the help of ligaments and muscles, to support the load and help perform more natural exercise.

However, in the case where it is hard to perform a motion by the natural knee joint due to arthritis caused by aging or various diseases, and knee damage caused by external impact, surgical procedures of implanting an artificial knee joint can be used to achieve the function according to the above mechanism of knee motion.

Generally, the artificial knee joint is roughly constituted by a thighbone coupling member, a tibia coupling member, a bearing member, and a knee coupling member, and it can take various forms in structure, material, surface treatment process, etc., of which a PS type artificial knee joint that is used when a posterior cruciate ligament is removed is configured such that the bearing member includes a post functioning as the posterior cruciate ligament, and the thighbone coupling member includes cam allowing smooth rotation by being engaged with the post, wherein based on the post of the bearing member, the direction in which the knee coupling member is located is defined as anterior and the direction in which the cam of the thighbone coupling member is engaged with the post is defined as the posterior of the artificial knee joint, and in the following description of the present invention and drawings, if the front and rear are to be indicated, they should be denoted by A and P respectively.

Further, in the process of performing a motion after the surgery of the PS type artificial knee joint, when the thighbone coupling member is severely bent backward by a rollback motion in which the femur bends backward, a gap between the post and the cam that were in contact with each other is increased and may not be restored, resulting in eventual dislocation. When the dislocation of the thighbone coupling member occurs, the artificial knee joint is unable to perform normally until it is re-operated on, and thus preventing dislocation is a very important task that must be achieved in the artificial knee joint field.

Further, in relation to the problem of the dislocation of a thighbone coupling member, when dislocation begins to occur, a maximum gap of the post and cam is referred to as a jump distance, and to prevent dislocation, it is advantageous to increase the jump distance as much as possible, but simply increasing the height of the post may result in increased wear of the bearing member or increased amount of bone to be cut in knee replacement surgery. Hereinbelow, the problem of the conventional artificial knee joint will be described in detail with reference to FIGS. 1 and 2.

FIG. 1 shows a conventional artificial knee joint, wherein as shown in FIG. 1(a), a post 31a is configured such that an upper surface is not inclined, and a posterior vertical surface is formed to be linear, so a jump distance D1 is low, whereby as shown in FIG. 1(b), it has a structure in which it is difficult to prevent dislocation of the thighbone coupling member 1, and since the upper surface of the post 31b is in a horizontal plane, it is difficult for the thighbone coupling member to be restored to a normal state after it is dislocated. In FIG. 1(c), a dark shaded area below a dotted line indicates the amount of bone to be cut in knee replacement surgery.

FIG. 2 shows the case of simply increasing the height of the post in the conventional artificial knee joint of FIG. 1, wherein as shown in FIG. 2(a), the basic shape of a post 31b is the same as the conventional artificial knee joint of FIG. 1, but by increasing the height of the post, a jump distance D2 is larger than the jump distance D1 of the conventional artificial knee joint.

Accordingly, as shown in FIG. 2(b), the dislocation prevention effect of the thighbone coupling member is improved compared to the conventional artificial knee joint of FIG. 1, but as shown in FIG. 2(c), when a cam 13 of a thighbone coupling member 1 is dislocated, it is difficult for the thighbone coupling member to be restored to a normal state since an upper surface of the post 31b is formed in a horizontal plane.

Further, the amount of bone to be cut in knee replacement surgery is further increased by a dark shaded area shown in FIG. 2(d) compared to the amount of bone to be cut shown in FIG. 1(c).

Thereby, to solve the above problem of dislocation of the thighbone coupling member, a stop member is provided inside the thighbone coupling member, or the cam is placed higher from anterior toward upward.

PATENT DOCUMENT

U.S. Pat. No. 5,824,100 (Oct. 20, 1998) "Knee prosthesis with increased balance and reduced bearing stress"
Korean Patent No. 10-0930727 (Dec. 9, 2009) "Artificial knee joint having advanced post and advanced cam"

However, the conventional techniques for preventing dislocation are problematic in that it increases wear of the bearing member, or it requires more bone to be cut in knee replacement surgery as in the case of simply increasing a height of the post in FIG. 2.

Accordingly, there is a need for an artificial knee joint having a structure that is capable of preventing dislocation with less bone to be cut while not increasing wear caused by use between the tibia coupling member and the bearing member.

DISCLOSURE

Technical Problem

Accordingly, the present invention has been made keeping in mind the above problems occurring in the related art, and an object of the present invention is to provide an artificial knee joint configured to include a post having a structure capable of preventing dislocation in the movement of the post of a bearing member and a cam of a thighbone coupling member.

Another object of the present invention is to provide an artificial knee joint having a structure that is capable of increasing a jump distance in the movement between the post and the cam without increasing an amount of bone required to be cut in knee replacement surgery.

A further object of the present invention is to provide an artificial knee joint having a structure that is capable of increasing a jump distance in the movement between the post and the cam without additional wear of the bearing member.

Still another object of the present invention is to provide an artificial knee joint configured such that an upper surface of the post, which is disposed at an upper portion of the post to perform a motion relative to the cam of the thighbone coupling member, is inclined at a predetermined angle, thereby having a structure that is capable of being restored naturally when the thighbone coupling member is dislocated.

Still another object of the present invention is to provide an artificial knee joint including an upper curved surface extending posteriorly from the upper surface and a lower curved surface with an inflection point existing therebetween, wherein a radius of curvature of the lower curved surface is larger than that of the upper curved surface, such that the thighbone coupling member ascends the inflection point existing between the upper curved surface and the lower curved surface, thereby preventing dislocation from the bearing member.

Still another object of the present invention is to provide an artificial knee joint configured such that the upper surface is inclined at a predetermined angle, and the radius of curvature of the lower curved surface is larger than that of the upper curved surface, thereby preventing dislocation of a thighbone coupling member and facilitating restoration when dislocated.

Objects of the present invention are not limited to the above objects, and other and further objects of the present invention will become obvious upon understanding of embodiments about to be described. Further, the objects of the present invention may be realized by means and combinations thereof indicated in the appended claims.

Technical Solution

In order to achieve the above objects, the present invention is realized by embodiments having the following configuration.

According to an embodiment of the present invention, an artificial knee joint capable of preventing dislocation of a thighbone coupling member includes: a thighbone coupling member; and a bearing member, wherein the bearing member includes a post having a contact surface at which the post is in contact with the thighbone coupling member, the thighbone coupling member includes a cam performing a cam motion relative to the post of the bearing member, the post includes an upper surface at which the post performs a motion relative to the cam of the thighbone coupling member, and the upper surface is inclined at a predetermined angle.

According to another embodiment of the present invention, in the artificial knee joint capable of preventing dislocation of a thighbone coupling member according to the present invention, the upper surface may be inclined such that a height thereof is gradually reduced from anterior to posterior.

According to a further embodiment of the present invention, the post may further include: an upper curved surface extending posteriorly from the upper surface; and a lower curved surface extending continuously from the upper curved surface, wherein the upper curved surface and the lower curved surface have respective centers of curvature that are disposed opposite to each other based on an inflection point existing therebetween.

According to still another embodiment of the present invention, in the artificial knee joint capable of preventing dislocation of a thighbone coupling member according to the present invention, the center of curvature of the lower curved surface may be disposed posteriorly based on the inflection point, and the center of curvature of the upper curved surface may be disposed anteriorly based on the inflection point.

According to still another embodiment of the present invention, in the artificial knee joint capable of preventing dislocation of a thighbone coupling member according to the present invention, a radius of curvature of the lower curved surface may be larger than that of the upper curved surface.

According to still another embodiment of the present invention, an artificial knee joint capable of preventing dislocation of a thighbone coupling member includes: a thighbone coupling member; and a bearing member, wherein the bearing member includes a post having a contact surface at which the post is in contact with the thighbone coupling member; the thighbone coupling member includes a cam performing a cam motion relative to the post of the bearing member; and the post includes an upper surface at which the post performs a motion relative to the cam of the thighbone coupling member, an upper curved surface extending posteriorly from the upper surface, and a lower curved surface extending continuously from the upper curved surface, wherein the upper curved surface and the lower curved surface have respective centers of curvature that are disposed opposite to each other based on an inflection point existing therebetween.

Advantageous Effects

The present invention can achieve the following effects according to the above embodiments, configuration, combination, and use relationship described below.

The present invention may prevent dislocation in the movement of the post of a bearing member and a cam of a thighbone coupling member.

The present invention may increase a jump distance in the movement between the post and the cam without increasing an amount of bone required to be cut in knee replacement surgery.

The present invention may increase a jump distance in the movement between the post and the cam without additional wear of the bearing member.

The present invention may be restored naturally when the thighbone coupling member is dislocated since it is configured such that an upper surface of the post, which is disposed at an upper portion of the post to perform a motion relative to the cam of the thighbone coupling member, is inclined at a predetermined angle.

The present invention includes an upper curved surface extending posteriorly from the upper surface and a lower curved surface with an inflection point existing therebetween, wherein a radius of curvature of the lower curved surface is larger than that of the upper curved surface, such that the thighbone coupling member ascends the inflection point existing between the upper curved surface and the lower curved surface, thereby preventing dislocation from the bearing member.

The present invention may increase stability and life in the movement of an artificial knee joint since it is configured such that the upper surface is inclined at a predetermined angle, and the radius of curvature of the lower curved surface is larger than that of the upper curved surface, thereby preventing dislocation of a thighbone coupling member and facilitating restoration when dislocated.

BEST MODE

Hereinafter, an artificial knee joint capable of preventing dislocation of a thighbone coupling member according to the present invention will be described in detail with reference to the accompanying drawings. Unless otherwise defined, all technical terms used herein have the same meaning as commonly understood by one of ordinary skill in the art to which this invention belongs, but if the meaning of the terms used herein is not consistent with the meaning commonly used, it will be interpreted according to the definition used in the specification. Further, in the following description of the invention, if the related known functions or specific instructions on configuring the gist of the present invention unnecessarily obscure the gist of the invention, the detailed description thereof will be omitted.

Throughout the specification, when a unit is referred to as "comprising" or "including" at least one component, it does not exclude other components unless stated otherwise and shall be referred to as comprising or including the other components.

An artificial knee joint capable of preventing dislocation of a thighbone coupling member according to an embodiment of the present invention will be described in detail with reference to FIGS. 3 to 6.

Figure 3:
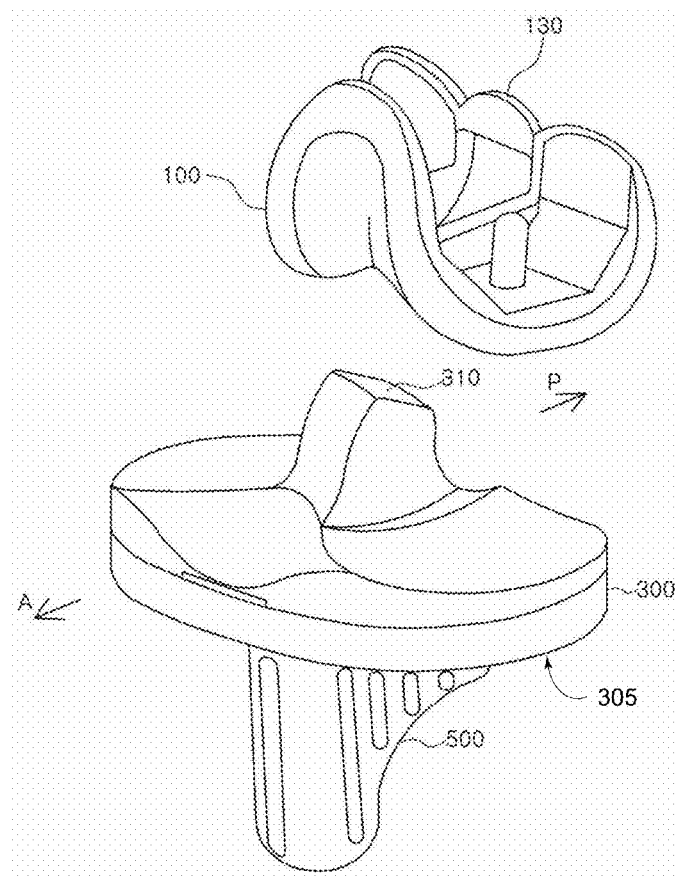
FIG. 3 shows a perspective view of the artificial knee joint according to an embodiment of the present invention.
Figure 4:
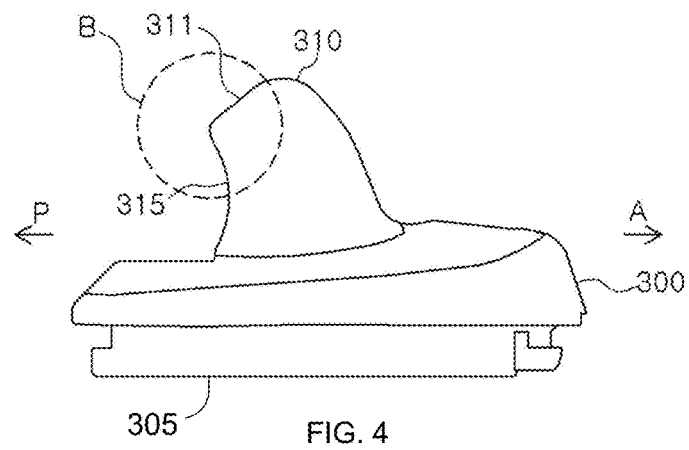
FIG. 4 shows a sectional view of a bearing member of the artificial knee joint according to an embodiment of the present invention.

As shown in FIG. 3, the artificial knee joint capable of preventing dislocation of a thighbone coupling member includes: a thighbone coupling member 100 coupled to a distal end of the femur; a bearing member 300 disposed between the thighbone coupling member and a tibia coupling member; and a tibia coupling member 500 having a proximal end coupled to a distal surface 305 of the bearing member 300. A distal end of the coupling member 500 is configured to be coupled to a proximal end of the tibia. The distal surface 305 of the bearing member 300 is at least partially flat, extending anteriorly A and posteriorly B, as indicated in FIG. 4, when distal surface 305 is disposed in a horizontal plane.

The thighbone coupling member 100 is configured such that a lower end thereof comes into contact with an upper end of the bearing member 300, and moves along with the bearing member during knee movement, wherein the thighbone coupling member includes a cam 130 that comes into direct contact with the bearing member 300.

The cam 130 is provided at a lower end of the thighbone coupling member 100, and serves to allow smooth rotations of thighbone coupling member 100 and to prevent dislocation by being engaged with a post 310 of the bearing member 300.

The bearing member 300 is disposed between the thighbone coupling member 100 and the tibia coupling member 500, and includes a post 310 functioning as an alternative to the posterior cruciate ligament.

Figure 5:
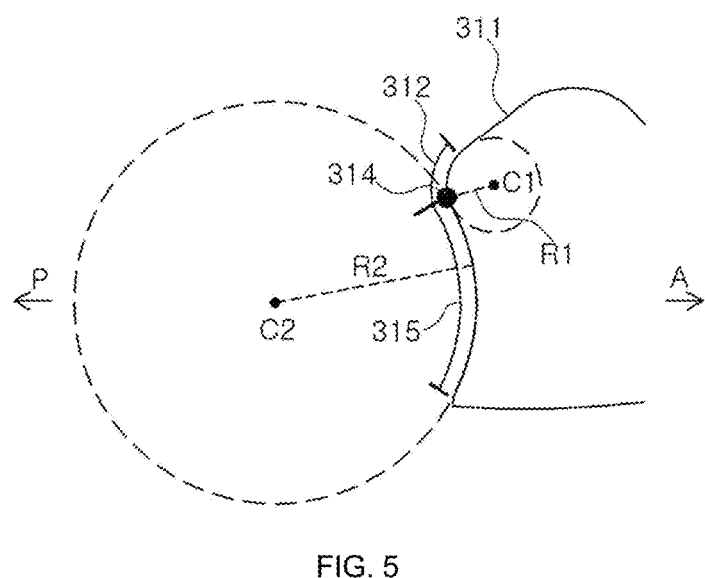
FIG. 5 shows an enlarged sectional view of A in the a post of the bearing member according to an embodiment of the present invention of FIG. 4.

As shown in FIGS. 4 to 6, the post 310 is a protruding part from an upper portion of the bearing member 300, and allows the cam 130 to be rotated by being engaged with the post 310 in movement of the thighbone coupling member 100, thereby functioning as an alternative to the posterior cruciate ligament, wherein the post includes: the an upper surface 311 disposed at an upper portion of the post; an upper curved surface 312 disposed right under the upper surface 311; an anterior surface 313 disposed anteriorly to the bearing member 300; an inflection point 314 disposed at a lower end of the upper curved surface 312; and a lower curved surface 315 disposed right under the inflection point 314.

The upper surface 311 is a surface that is disposed at an upper portion of the post 310, is formed to be inclined, but not be horizontal in the conventional artificial knee joint, and is configured such that a height thereof is gradually reduced as approaching the post 10 from anterior to posterior, whereby as shown in FIG. 6 (c), even if the cam 130 is temporarily dislocated due to excessive rotation of the thighbone coupling member 100, the upper surface guides the cam 130 to descend along the upper surface 311 to be restored from a dislocation state to a normal state, and thus it is possible to improve the life and stability of an artificial knee joint.

The upper curved surface 312 is a curved surface having the inflection point 314 as its lower end by extending posteriorly from the upper surface 311, and a radius of curvature R1 of the upper curved surface 312 is smaller than a radius of curvature R2 of the lower curved surface 315, whereby as shown in FIG. 6 (b), even if the thighbone coupling member 100 is bent posteriorly and the cam 130 being moved at the lower curved surface 315 is moved up, the cam is stopped by the inflection point 314, thereby having a structure that firstly prevents dislocation from the bearing member 300.

Further, even if the thighbone coupling member 100 is further bent and the cam 130 is temporarily dislocated, as in the description of the upper surface 311, the cam 130 is guided to descend along the upper surface 311 to be restored from a dislocation state to a normal state, thereby secondly preventing dislocation of the thighbone coupling member.

The anterior surface 313 is a part that extends anteriorly from the upper surface 311, is connected to an anterior portion of the bearing member 300, and may be formed with a gently curved surface.

Figure 6A:
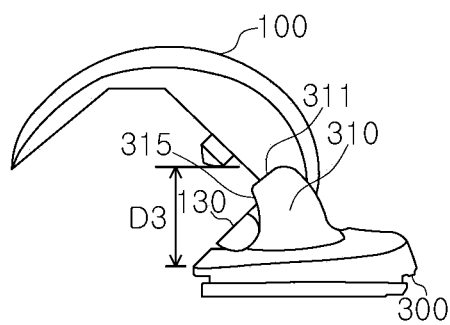
FIG. 6(a) shows sectional views of an embodiment of an inventive artificial knee joint in a normal state.
Figure 6B:
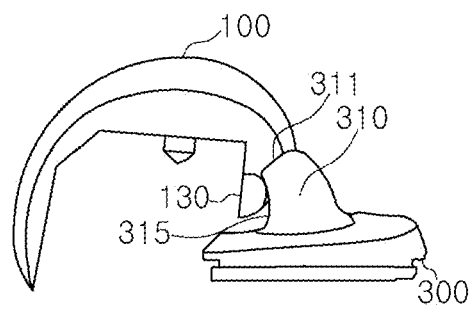
FIG. 6(b) shows the artificial knee joint of FIG. 6(a) in a rollback state.

The inflection point 314 is a point at which the curvature changes between the upper curved surface 312 and the lower curved surface 315, and based on the inflection point, the radius of curvature R1 of the upper curved surface 312 is smaller than the radius of curvature R2 of the lower curved surface 315, such that the curvature changes dramatically, whereby as shown in FIG. 6(b), it is possible to efficiently prevent the cam 130 from being dislocated from the post 310.

The lower curved surface 315 is a curved surface extending downward from the inflection point 314 to a posterior direction, and is configured such that even if the thighbone coupling member 100 is bent posteriorly, the cam 130 is moved along the lower curved surface 315, thereby facilitating smooth rotations. As shown in FIG. 5, the lower curved surface 315 is configured such that a center C1 of curvature of the upper curved surface is disposed anteriorly based on the inflection point 314, and a center C2 of curvature of the lower curved surface is disposed posteriorly based on the inflection point 314, whereby a movement radius of the cam 130 is within the range of the lower curved surface 315, and is stopped by the inflection point 314 when the thighbone coupling member 100 is bent posteriorly, thereby having a structure that prevents dislocation of the thighbone coupling member 100.

The tibia coupling member 500 is a part that is disposed at the lower portion of the bearing member 300, and is configured such that an upper portion thereof allows the bearing member 300 to be seated thereon, and a lower portion thereof serves to fix the tibia by being coupled thereto, wherein the tibia coupling member 500 is roughly divided into a cemented type to improve bonding strength with tibia and a cementless type without bone cement, and it may have various structures for bonding with other tibia and for internal fixation.

Hereinbelow, the present invention is compared with the conventional artificial knee joint, and the case of increasing the height of the post in the conventional artificial knee joint, respectively, and a dislocation problem occurring when the thighbone coupling member is bent posteriorly, and the amount of bone required to be cut in knee replacement surgery will be described in detail with reference to FIGS. 1 to 8.

Figure 1A:
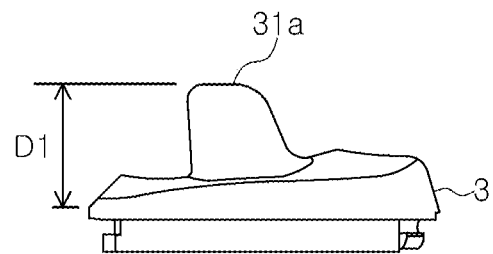
FIG. 1(a) shows a reference view of a structure of a conventional artificial knee joint.
Figure 1B:
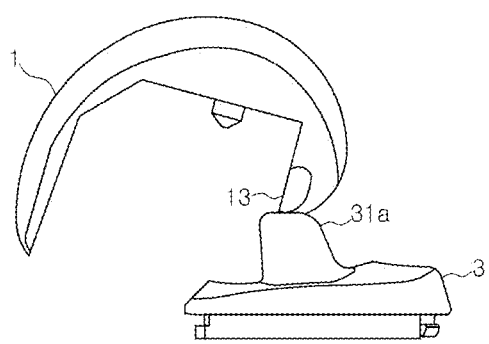
FIG. 1(b) shows the artificial knee joint of FIG. 1(a) during a rollback exercise.
Figure 1C:
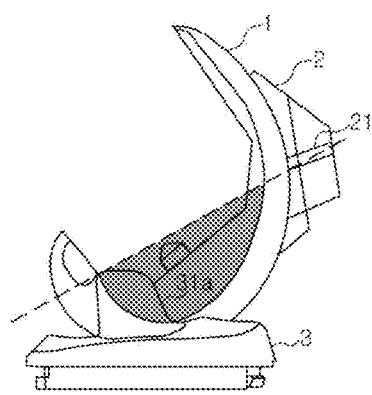
FIG. 1(c) shows an amount of bone to be cut in knee replacement surgery using the conventional artificial knee joint.

In the case of the conventional artificial knee joint, as shown in FIG. 1(a), a post 31a is configured such that an upper surface is not inclined, and a posterior vertical surface is formed to be linear, so a jump distance D1 is low, whereby as shown in FIG. 1(b), it has a structure, in which it is difficult to prevent dislocation of the thighbone coupling member 1, and since the upper surface of the post 31b is in a horizontal plane, it is difficult for the thighbone coupling member to be restored to a normal state after it is dislocated. In FIG. 1(c), a dark shaded area below a dotted line indicates the amount of bone to be cut in knee replacement surgery.

Figure 2A:
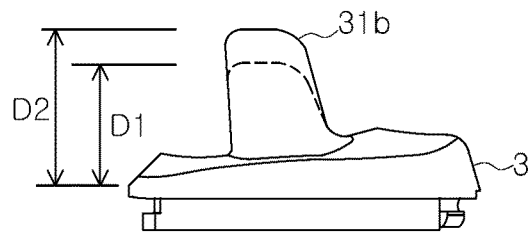
FIG. 2(a) shows a reference view of a structure in the case of simply increasing a height of a post in order to increase a jump distance of the conventional artificial knee joint shown in FIG. 1(a)

Further, the case of simply increasing the height of the post in the conventional artificial knee joint, as shown in FIG. 2(a), the basic shape of a post 31b is the same as the conventional artificial knee joint of FIG. 1, but by increasing the height of the post, a jump distance D2 is increased.

Figure 2B:
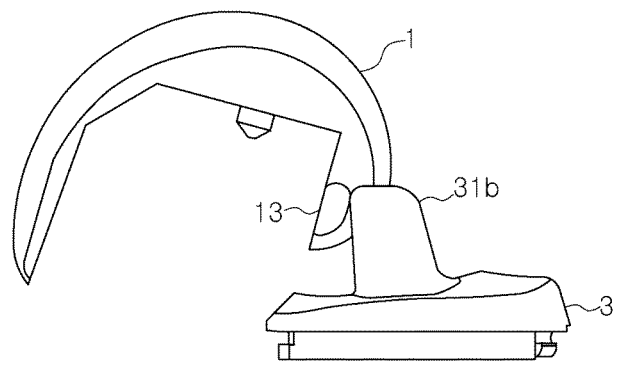
FIG. 2(b) and FIG. 2(c) show a state of the knee joint in FIG. 2(a) during a rollback exercise.
Figure 2C:
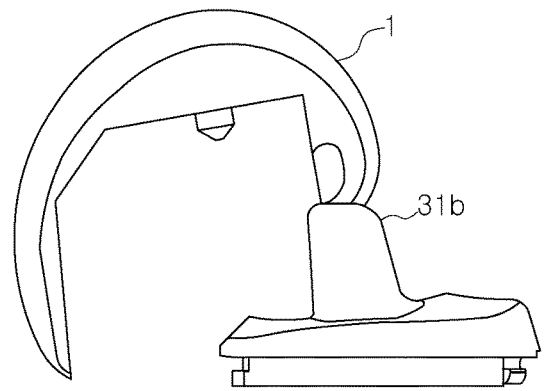

Accordingly, as shown in FIG. 2(b), the dislocation prevention effect of the thighbone coupling member is improved compared to the conventional artificial knee joint of FIG. 1, but as shown in FIG. 2(c), when a cam 13 of a thighbone coupling member 1 is dislocated, it is difficult for the thighbone coupling member to be restored to a normal state since an upper surface of the post 31b is formed in a horizontal plane.

Figure 2D:
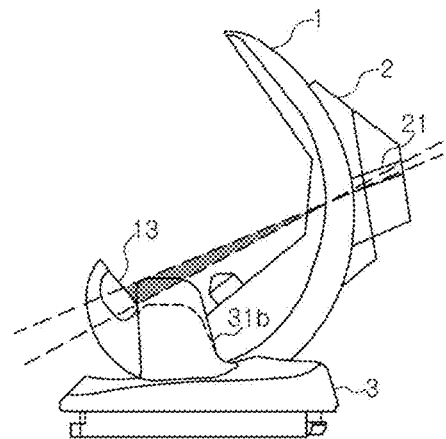
FIG. 2(d) shows an amount of bone to be cut in knee replacement surgery using the knee joint of FIG. 2(a)

Further, as shown in FIG. 2(d), the amount of bone to be cut in knee replacement surgery is considerably increased compared to the amount of bone to be cut shown in FIG. 1(c).

Figure 6C:
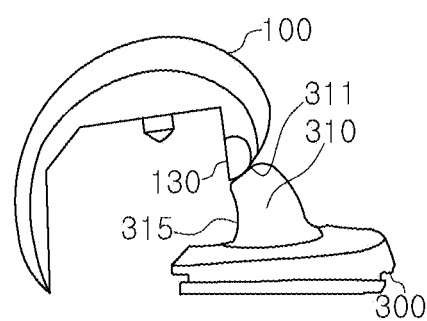
FIG. 6(c) shows the artificial knee joint of FIG. 6(a) in a dislocation state, depending on the motion state of a thighbone coupling member.

On the contrary, in the case of the present invention, as shown in FIG. 6(a), the inclined upper surface 311 and the lower curved surface 315 are provided and the jump distance D2 is increased; as shown in FIG. 6(b), the dislocation prevention effect of the thighbone coupling member 100 is improved compared to FIG. 1(b); as shown in FIG. 6(c), even when the cam 130 of the thighbone coupling member 100 is dislocated, the cam 130 descends along the upper surface 311, thereby facilitating restoration when dislocated, and through this, it is possible to prevent wear of the bearing member occurring in the restoration process when the thighbone coupling member 100 is dislocated.

Figure 7A:
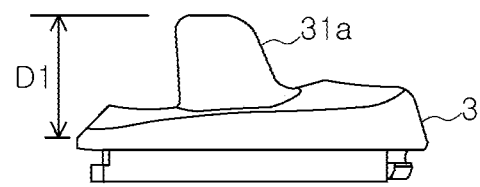
FIG. 7(a) shows sectional views of structures of the conventional artificial knee joint.
Figure 7B:
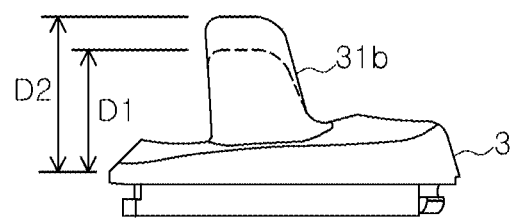
FIG. 7(b) shows a case of simply increasing the height of the post in the conventional artificial knee joint shown in FIG. 7(a)
Figure 7C:
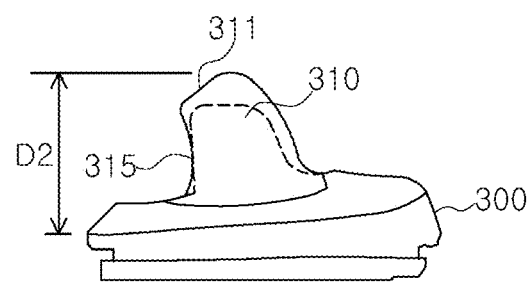
FIG. 7(c) shows sectional views of structures of one embodiment of the inventive knee joint.

Further, in terms of the jump distance of the artificial knee joint, as shown in FIG. 7, in the conventional artificial knee joint (a), the lower jump distance D1 is lower; in the case of simply increasing the height of the post in the conventional artificial knee joint (b), the jump distance D2 is increased, but it is difficult to efficiently prevent dislocation of the thighbone coupling member and is difficult to restore the thighbone coupling member when dislocated. In the case of the present invention (c), it is possible to prevent dislocation of a thighbone coupling member while increasing the jump distance D2, and the amount of bone to be cut is not increased, which will be described in detail with reference to FIGS. 8 to 10, hereinbelow.

Figure 8A:
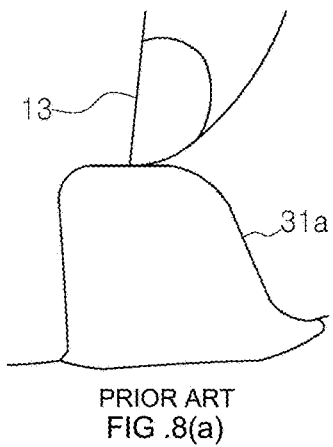
FIG. 8(a) shows enlarged sectional views of the conventional artificial knee joint in FIG. 1(b) in cam motions.
Figure 8B:
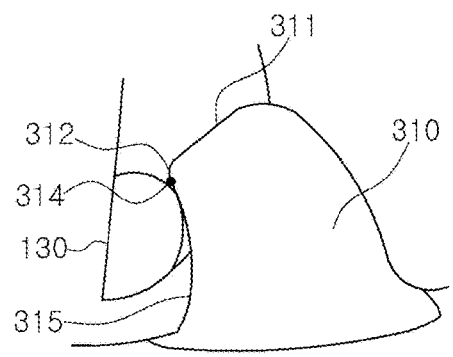
FIG. 8(b) shows the present invention in cam motions in FIG. 6(b) showing a case where the thighbone coupling member is bent posteriorly.

FIG. 8 shows enlarged views of cam motions in a case where the thighbone coupling member is bent posteriorly, wherein the conventional artificial knee joint (a) has a structure in which it is difficult to prevent dislocation of the cam 13 when the thighbone coupling member is bent posteriorly, and on the contrary, the present invention (b) may firstly prevent dislocation of the thighbone coupling member since it is configured such that the cam 130 is stopped by the inflection point 314 by being prohibited from approaching the upper curved surface 312 over the lower curved surface 314.

Figure 9A:
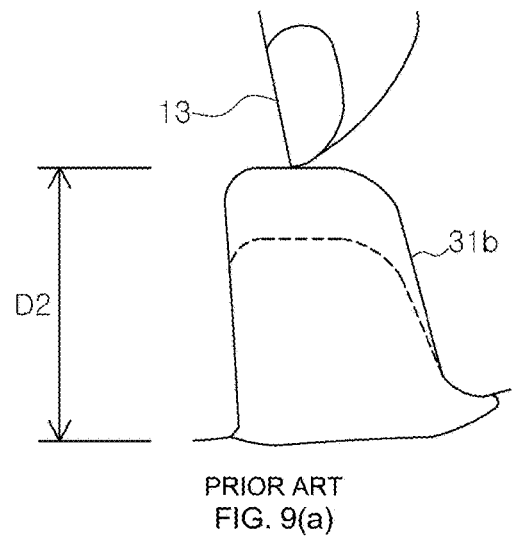
FIG. 9(a) shows enlarged sectional views of the case of simply increasing the height of the post in the conventional artificial knee joint in cam motions in FIG. 2(c) showing a case where the thighbone coupling member is dislocated.
Figure 9B:
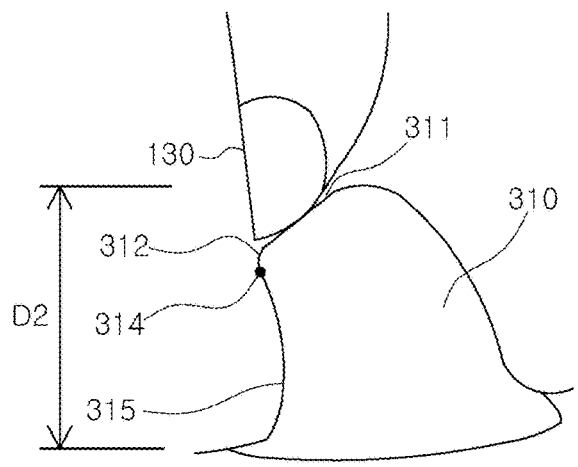
FIG. 9(b) shows the present invention in cam motions in FIG. 6(c) showing a case where the thighbone coupling member is dislocated.

FIG. 9 shows enlarged views of cam motions in a case where the thighbone coupling member is dislocated, wherein in the case of simply increasing the height of the post in the conventional artificial knee joint (a), since the upper surface of the post 31b is in a horizontal plane, it is difficult for the thighbone coupling member to be restored to a normal state after it is dislocated in cam motions. On the contrary, in the case of the present invention (b), since the cam 130 has a structure easily descending along the upper surface 311 that is inclined from anterior to posterior, it is easy to restore the thighbone coupling member when dislocated.

Figure 10A:
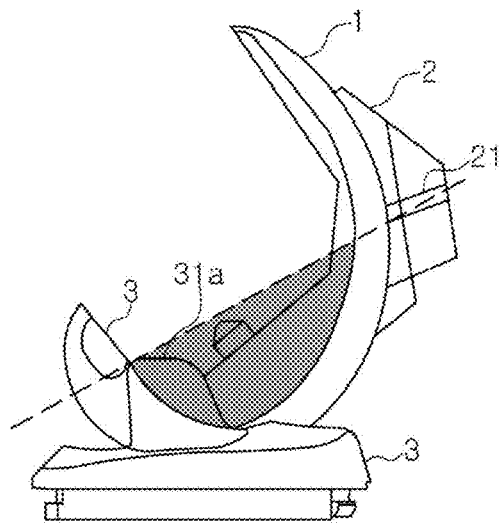
FIG. 10(a) shows side sectional views of structures of the conventional artificial knee joint relating to the amount of bone to be cut in knee replacement surgery.
Figure 10B:
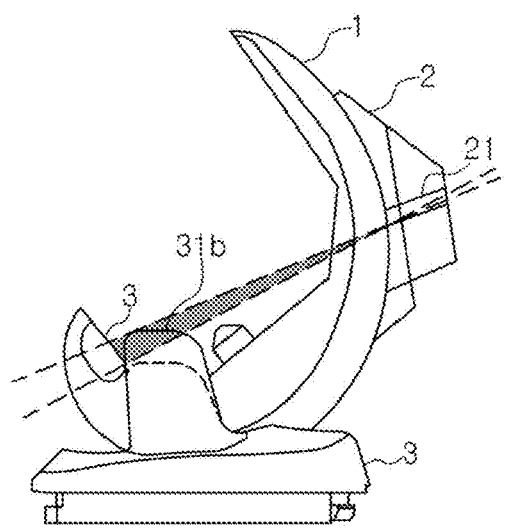
FIG. 10(b) shows the case of simply increasing the height of the post in the conventional artificial knee joint relating to the amount of bone to be cut in knee replacement surgery.
Figure 10C:
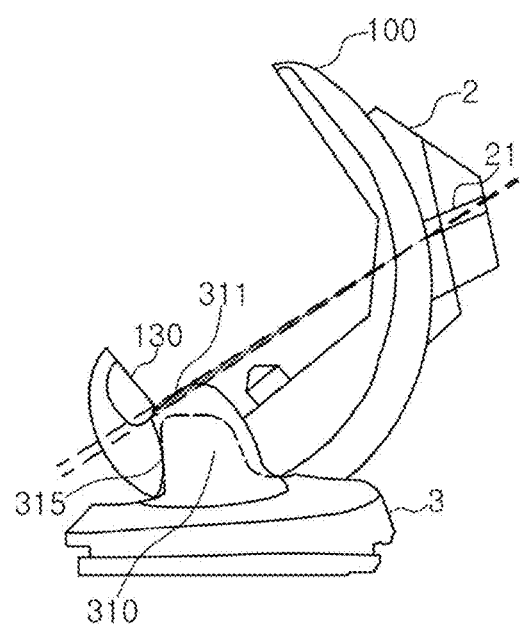
FIG. 10(c) shows the present invention relating to the amount of bone to be cut in knee replacement surgery.

FIG. 10 shows amounts of bone to be cut in knee replacement surgery, wherein an amount of bone to be cut (b) in the case of simply increasing the height of the post is significantly increased compared to an amount of bone to be cut (a) in the conventional artificial knee joint, but an amount of bone to be cut(c) in the present invention is only slightly increased. Accordingly, the present invention has a structure that is capable of increasing a jump distance without increasing an amount of bone to be cut.

In the above description, although reference to the preferred embodiments has allowed the present invention to be described in more detail, it should be understood that the present invention is intended to cover not only the exemplary embodiments, but also various alternatives, modifications, equivalents and other embodiments that may be included within the spirit and scope of the present invention as defined by the appended claims.

The invention claimed is:

1. An artificial knee joint comprising:
a thighbone coupling member; and
a bearing member having a distal surface disposed in a horizontal plane and extending anteriorly and posteriorly, the bearing member also including a post having a contact surface in contact with the thighbone coupling member, the contact surface of the post further comprising:
an upper surface;
an upper curved surface extending posteriorly from the upper surface;
a lower curved surface extending continuously from the upper curved surface; and
an inflection point between the upper curved surface and the lower curved surface,
wherein:
a radius of curvature of the lower curved surface is larger than a radius of curvature of the upper curved surface;
the lower curved surface has a center of curvature disposed posteriorly to the inflection point; and
the upper curved surface has a center of curvature disposed anteriorly to the inflection point such that the upper curved surface protrudes posteriorly of the inflection point.

2. The artificial knee joint of claim 1, wherein the upper surface is inclined such that a height thereof is gradually reduced from anterior to posterior.

3. An artificial knee joint comprising:
a thighbone coupling member; and
a bearing member having a distal surface extending anteriorly and posteriorly, wherein
the bearing member includes a post having a contact surface in contact with the thighbone coupling member;
the thighbone coupling member includes a cam performing a cam motion relative to the post of the bearing member; and
the post includes an upper surface at which the post performs a motion relative to the cam of the thighbone coupling member, an upper curved surface extending posteriorly from the upper surface, and a lower curved surface extending continuously from the upper curved surface, wherein the upper curved surface and the lower curved surface have respective centers of curvature that are disposed opposite an inflection point existing therebetween,
the center of curvature of the lower curved surface is disposed posteriorly to the inflection point,
the center of curvature of the upper curved surface is disposed anteriorly to the inflection point, and
a radius of curvature of the lower curved surface is larger than that of the upper curved surface such that the upper curved surface protrudes posteriorly of the inflection point.

4. The artificial knee joint of claim 1, wherein a vertical plane projecting orthogonal to the horizontal plane passes through the inflection point, the center of curvature of the lower curved surface being disposed posteriorly to the vertical plane, and the center of curvature the upper curved surface being disposed anteriorly to the vertical plane such that the upper curved surface protrudes posteriorly of the vertical plane.

5. An artificial knee joint comprising:
a thighbone coupling member comprising a cam having a cam surface, the cam surface being completely convex; and
a bearing member that includes a post having a contact surface in contact with the cam surface on at least a posterior side of the post, the contact surface of the post comprising:
an upper surface at which the post performs a motion relative to the cam of the thighbone coupling member;
an upper curved surface extending posteriorly from the upper surface;
a lower curved surface extending below and anteriorly from the upper curved surface; and
an inflection point disposed between the upper curved surface and the lower curved surface,
wherein:
the lower curved surface has a center of curvature disposed posteriorly to the inflection point; and the upper curved surface has a center of curvature disposed anteriorly to the inflection point such that the upper curved surface protrudes posteriorly over the inflection point.

6. The artificial knee joint of claim 5, wherein a radius of curvature of the lower curved surface is larger than a radius of curvature of the upper curved surface.

\* \* \* \* \*